United States Patent
Battiwalla

(10) Patent No.: US 11,944,453 B2
(45) Date of Patent: Apr. 2, 2024

(54) CLINICAL FITTING ASSISTANCE USING SOFTWARE ANALYSIS OF STIMULI

(71) Applicant: Cochlear Limited, Macquarie University (AU)

(72) Inventor: Xerxes Battiwalla, Sydney (AU)

(73) Assignee: Cochlear Limited, Macquarie University (AU)

( * ) Notice: Subject to any disclaimer, the term of this patent is extended or adjusted under 35 U.S.C. 154(b) by 659 days.

(21) Appl. No.: 16/944,406

(22) Filed: Jul. 31, 2020

(65) Prior Publication Data

US 2021/0007662 A1 Jan. 14, 2021

Related U.S. Application Data

(63) Continuation of application No. 13/907,058, filed on May 31, 2013, now Pat. No. 10,758,177.

(51) Int. Cl.
*A61B 5/00* (2006.01)
*H04R 25/00* (2006.01)

(52) U.S. Cl.
CPC .......... *A61B 5/4851* (2013.01); *A61B 5/0022* (2013.01); *A61B 5/0077* (2013.01); *A61B 5/486* (2013.01); *A61B 5/7264* (2013.01); *A61B 5/743* (2013.01); *A61B 5/7445* (2013.01); *A61B 5/746* (2013.01); *H04R 25/70* (2013.01); *H04R 2225/81* (2013.01)

(58) Field of Classification Search
CPC ................ A61B 5/4851; A61B 5/0022; A61B 5/0077; A61B 5/486; A61B 5/7264; A61B 5/743; A61B 5/7445; A61B 5/746; H04R 25/70; H04R 2225/81
See application file for complete search history.

(56) References Cited

U.S. PATENT DOCUMENTS

| | | | |
|---|---|---|---|
| 6,035,050 A | 3/2000 | Weinfurtner et al. | |
| 7,319,780 B2 | 1/2008 | Fedorovskaya et al. | |
| 7,908,011 B2 | 3/2011 | McMahon et al. | |
| 10,758,177 B2 | 9/2020 | Battiwalla | |
| 2005/0038680 A1 | 2/2005 | McMahon | |

(Continued)

FOREIGN PATENT DOCUMENTS

| | | |
|---|---|---|
| EP | 1703770 A1 | 9/2006 |
| WO | 2012010199 A1 | 1/2012 |
| WO | 2012101494 A2 | 8/2012 |

OTHER PUBLICATIONS

Ashraf, Ahmed Bilal, et al. "The painful face—pain expression recognition using active appearance models." Image and vision computing 27.12 (2009): 1788-1796.

(Continued)

*Primary Examiner* — David J. McCrosky
(74) *Attorney, Agent, or Firm* — Edell, Shapiro & Finnan, LLC

(57) ABSTRACT

Embodiments of the present disclosure identify and alert a clinician to physiological cues thereby aiding the clinician in providing a better fitting of a medical prosthesis. Physiological data of a recipient of a medical prosthesis is analyzed to identify triggers during fitting or other types of adjustments to the prosthesis. A determination is then made as to whether the identified triggers correspond to a feedback event. If the triggers correspond to a feedback event, an alert containing information about the feedback event is generated and displayed or otherwise made available to the clinician.

14 Claims, 7 Drawing Sheets

(56) References Cited

U.S. PATENT DOCUMENTS

| | | | |
|---|---|---|---|
| 2006/0153395 A1* | 7/2006 | van Den Heuvel | A61N 1/36039 381/60 |
| 2006/0204013 A1 | 9/2006 | Hannibal et al. | |
| 2007/0071262 A1 | 3/2007 | Rass | |
| 2009/0306743 A1 | 12/2009 | Van Den Heuvel | |
| 2010/0076339 A1 | 3/2010 | Marcoux | |
| 2010/0196861 A1 | 8/2010 | Lunner | |
| 2011/0091056 A1 | 4/2011 | Nishizaki et al. | |
| 2013/0121496 A1 | 5/2013 | Boretzki | |
| 2014/0023214 A1 | 1/2014 | Edgar | |
| 2014/0228909 A1 | 8/2014 | Dhanasingh et al. | |
| 2014/0270210 A1 | 9/2014 | van Dijk | |

OTHER PUBLICATIONS

Cochlear Implant Online, "Lisa Munson's Story". Oct. 18, 2012. Retrieved from <http://cochlearimplantonline.com/site/lisa-munsons-story> on Jun. 24, 2017.

Gorman, "Microsoft Kinect Learns to Read Hand Gestures, Minority Report-Style Interface Now Possible", IEEE Spectrum online, Mar. 13, 2013. Retrieved from <http://spectrum.ieee.org/automaton/robotics/robotics-software/microso- ft-kinect-hand-gesture-control> on Apr. 23, 2015.

Gross, "Fitting Techniques for the Pediatric Cochlear Implant Patient", Audiology Online. May 12, 2003. Retrieved from <http://www.audiologyonline.com/articles/fitting-techniques-for-pediat- ric-cochlear-1128> on Jun. 24, 2017.

Koelewijn, Thomas et al., "Pupil Dilation Uncovers Extra Listening Effort in the Presence of a Single-Talker Masker", Ear & Hearing, 2012, vol. 33, No. 2, pp. 291-300.

Monwar, Md Maruf, and Siamak Rezaei. "Pain recognition using artificial neural network." Signal Processing and Information Technology, 2006 IEEE International Symposium on. IEEE, 2006.

Prkachin, Kenneth M. "Assessing pain by facial expression: facial expression as nexus." Pain Research and Management 14.1 (2009): 53-58.

Prkachin, Kenneth M. "The consistency of facial expressions of pain: a comparison across modalities." Pain 51.3 (1992): 297-306.

* cited by examiner

CLINICAL FITTING ASSISTANCE USING SOFTWARE ANALYSIS OF STIMULI

CROSS-REFERENCE TO RELATED APPLICATIONS

This application is a continuation of U.S. Non-Provisional Patent Application No. 13/907,058, filed May 31, 2013, now U.S. Pat. No. 10,758,177, entitled, "Clinical Fitting Assistance Using Software Analysis of Stimuli". The disclosure of this priority application is hereby incorporated by reference in its entirety into the present application.

BACKGROUND

Medical science has developed many different medical prostheses to address different ailments and impairments of recipients. Often, a medical prosthesis is calibrated or tuned for a particular recipient to match the recipient's needs and ensure the recipient's comfort. Such tuning or adjustment is referred to as "fitting" the medical prosthesis to the recipient. In many instances, physiological cues can be used to aid a clinician during the fitting process. However, such cues are often missed by clinicians performing the fitting due to lack of experience of the clinician or because the attention of the clinician is focused on the medical prosthesis or other tools for tuning, rather than on the recipient. It is with respect to this general environment that embodiments of the present disclosure have been contemplated.

SUMMARY

Embodiments of the present disclosure identify and alert a clinician to physiological cues thereby aiding the clinician in providing a better fitting of a medical prosthesis. Physiological data of a recipient of a medical prosthesis is analyzed to identify triggers during fitting or other types of adjustments to the prosthesis. A determination is then made as to whether the identified triggers correspond to a feedback event. If the triggers correspond to a feedback event, an alert containing information about the feedback event is generated and displayed or otherwise made available to the clinician.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

The systems and methods disclosed herein relate to providing clinical fitting assistance using visual or other stimuli. In many circumstances, a recipient of a medical prosthesis requires a clinician, technician, or physician, collectively referred to hereafter as a "clinician," to fit or otherwise tune or adjust the prosthesis to the particular needs of the recipient. Fitting the medical prosthesis is often required to ensure optimal use and comfort for the recipient. Sometimes, but not all the time, software is employed to help the clinician appropriately fit the medical prosthesis. Physiological cues can aid the clinician in correctly fitting the medical prosthesis by providing a clue to any pain, discomfort, or other reaction that the recipient is experiencing due to operation of the medial prosthesis. The physiological cues play an even more important role in fitting a prosthesis when the recipient is mentally disabled, an infant or child, or otherwise unable to convey their discomfort the clinician. During the fitting, it is often the case that the clinician is focused on the medical prosthesis or the fitting software, thereby missing physiological cues of the recipient during the fitting. Lack of experience can also result in the clinician missing physiological cues that could aid in a better fitting.

Embodiments of the present disclosure identify and alert a clinician to physiological cues thereby aiding the clinician in providing a better fitting of the medical prosthesis as well as providing a tool that a clinician can use to become more competent at performing fittings. For simplicity of illustration, embodiments of the present disclosure will be described with respect to fitting a hearing prosthesis such as, but not limited to, a cochlear implant, a hearing aid, a direct acoustic simulator, an active or passive transcutaneous bone conduction device, an auditory brainstem implant, middle ear devices that directly stimulate a middle ear structure such as the ossicular chain, tooth anchored hearing devices, etc. However, one of skill in the art will appreciate that the embodiments disclosed herein can be practiced with other types of medical prostheses, such as prosthetic limbs, artificial organs, etc. In embodiments, the systems and methods disclosed herein work in conjunction with fitting software or as a standalone system or module to identify and alert a clinician to the physiological cues of a recipient during fitting of a medical prosthesis. In further embodiments, in addition to identifying and alerting the clinician to the physiological cues, the embodiments disclosed herein can provide information about the physiological cue and/or information to the clinician about how to proceed with the fitting based upon the identified physiological cues.

Figure 1:
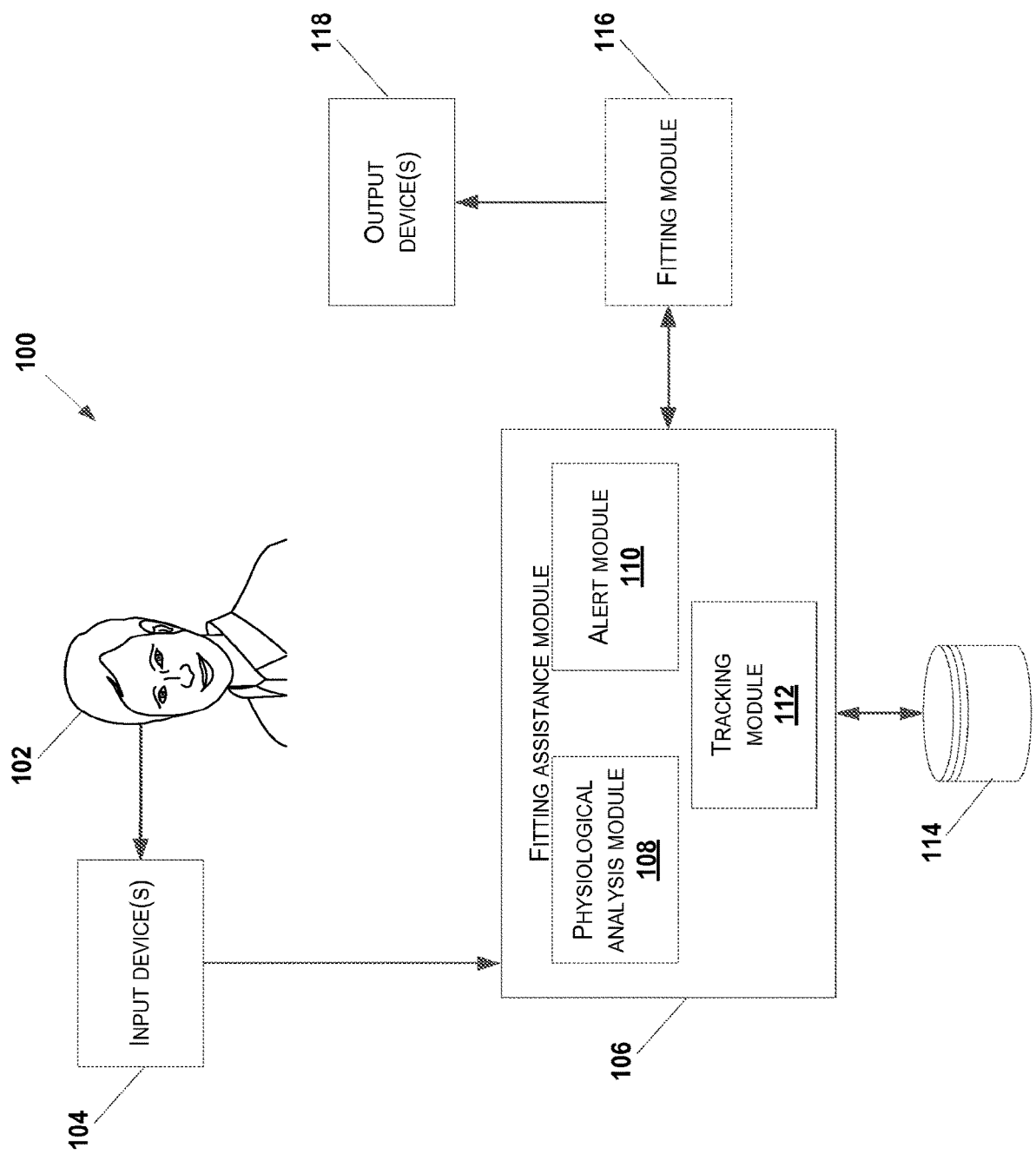
FIG. 1 is an embodiment of a system for providing medical prosthesis fitting assistance.

FIG. 1 is an embodiment of a system 100 for providing medical prosthesis fitting assistance. Specifically, the system 100 is employed to monitor the physiological cues of a medial prosthesis recipient 102. During the fitting process, the recipient 102 receives a plurality of stimuli (not shown in FIG. 1) designed to test the functionality of a medical prosthesis. In the case of fitting a hearing prosthesis, the stimulus is in the form of one or more auditory signals. Other types of stimuli can be applied to recipient 102 based on the type of medical prosthesis being tested. The recipient 102 is continually monitored by one or more input devices 104. Input devices 104 comprise one or more video cameras, microphones, heartbeat monitors, devices to measure blood pressure, or any other type of devices capable of monitoring the physiological responses of recipient 102. In one embodiment, one or more cameras can be used to identify the physical response of the recipient 102. The view of one or more cameras can be positioned on specific portions of the body to identify known cues. In one embodiment, any type of suitable camera can be used. However, in alternate embodiments, stereoscopic cameras are employed to provide depth perception. The use of depth perception can be used to enhance the detection of subtle changes in the recipient 102 such as a subtle twitch of the eye, a subtle movement, etc.

Input devices 104 are in electrical communication with fitting assistance module 106. In embodiments, input devices 104 can communicate with the fitting assistance module over a wired or wireless network. Any type of suitable network can be used to facilitate communication between input devices 104 and fitting analysis module 106 to facilitate communication of data from input device(s) 104 to fitting analysis module 106. Such networks include, but are not limited to, a WAN, a LAN, the Internet, or any other type of suitable network. Fitting analysis module 106 receives data from the one more input devices 106 and analyzes the data using physiological analysis module 108 to identify physiological responses from the recipient 102 that can aid in the fitting process. The physiological responses can act as a psychological trigger that can be used to identify problems with the fitting of the medical prosthesis. The type of analysis performed by the physiological analysis module 108 depends on the type of data received from the input device(s) 104. For example, if the input device(s) 104 comprise one or more cameras, the physiological analysis module 108 can perform video analysis and/or image analysis on individual frames to identify movements or other type of feedback events made by the recipient 102 to detect triggers that relate to the functioning of the medical prosthesis and/or the comfort of the recipient 102. In embodiments, the physiological analysis module 108 identifies a trigger and compares it to the stimulus applied to the recipient 102 to identify a particular feedback event. Data about the stimulus can be provided to the fitting assistance module 106 by a fitting module 116 or any other module or device that generates a stimulus for fitting purposes.

In embodiments, a number of different triggers can be identified by the physiological analysis module 108. Different types of triggers are identified based upon the input received from input device(s) 104. With respect to video received from one or more cameras monitoring the recipient 102 during fitting of a hearing prosthesis, identifiable triggers comprise eye-blink reflexes, facial nerve (Cranial VII) stimulation, sudden body movement, and/or pupil dilation. The eye-blink reflex is useful in determining loudness and/or discomfort level in infants and adults. The physiological analysis module 108 can detect such triggers by determining if a particular eye-movement reaction is close in time to a clinical stimulation action and thus, determine the eye-movement to be a result of the stimulation. Facial nerve stimulation comprises many different types of triggers. The facial nerve controls five major branches of sensation and mechanical reaction. Stimulation of the facial nerve due to excessive stimulation can present itself in a number of symptoms which could be used to determine if there is any information to present to the clinician during the fitting process. One type of facial nerve stimulation trigger is unintentional facial twitching. Unintentional facial twitching is useful in determining stimulation problems via an involuntary reflex. The physiological analysis module 108 determines if a twitch on the recipient's 102 face was close in time to a clinical stimulation action and this is determined to be as a result of the stimulation. Another type of facial stimulation trigger is a mouthing action. Mouthing actions are useful in determining stimulation problems through changes in taste sensations (e.g. a metallic taste). Mouthing actions captured by video footage can be used to help identify if a recipient is unknowingly experiencing a change in taste. Yet another type of facial nerve stimulation trigger is unexpected physical sensations. Unexpected physical sensations are useful in determining stimulation problems through physical sensations in the face or neck. A recipient subconsciously touching or rubbing these areas can indicate the recipient is experiencing abnormal stimulation. While specific facial nerve stimulation triggers are provided in this disclosure, the embodiments disclosed herein are capable of identifying other types of triggers for feedback events.

Another type of trigger that the physiological analysis module 108 can identify is a sudden body movement. A sudden body movement is useful in determining the softest sound that an infant has heard. The system would determine if the infant moved close in time to a clinical stimulation action and thus the reaction was determined to be as a result of the stimulation. Pupil dilation is yet another type of trigger that can be used to identify a feedback event. Pupil dilation is useful in determining the stress and effort levels involved in a listening activity. The system can examine changes in pupil dilation during the fitting process and suggest the clinician try an alternative task to allow the recipient time to recoup and perform at their peak. For ease of illustration, the disclosure has provided various different triggers that can be identified by the physiological analysis module 108 based on video input of a recipient provided during a fitting of a hearing prosthesis. One of skill in the art will appreciate that other types of triggers can be identified to determine different feedback events based upon the type of input received from input device(s) 104, the type of stimulation provided, and/or the type of medical prosthesis fitted to the recipient 102.

Fitting assistance module 106 can also comprise a tracking module 112 that can be used to record stimulus information and trigger information for a particular recipient 102. The tracking module saves such information, as well as feedback information and/or additional information provided by a clinician for a particular recipient that can be used in future fittings for the particular recipient. Such information can be saved in a datastore 114. Tracking allows the system 100 to save custom information that applies to the particular recipient. For example, tracking stimulus, trigger, and/or feedback information for recipients allows for the physiological analysis module 108 to accurately identify feedback events for particular recipients based upon their past fitting history. Furthermore, aggregation of such information from multiple recipients provides for the updating of the physiological analysis module by a machine learning algorithm. The machine learning algorithm monitors responses across a number of recipients over time to build a more detailed database of potential feedback events and different manifestations of known feedback events, thereby increasing the functionality and accuracy of the fitting assistance module over time.

In alternate embodiments, the clinician can review the feedback information and identify feedback events that that were not initially detected by the system 100. For example, the algorithm may miss a subtle feedback event or a reaction that is not known to be a trigger. The clinician can identify any missed feedback events, via interaction with a user interface, and such information can be stored and/or processed to update the physiological analysis module. For example, in such embodiments, the clinician could pause/rewind video footage (or otherwise interact or manipulate input device data) and identify/highlight key indicators in the data that will aid in a machine learning algorithm to update the physiological analysis module.

Upon detecting a trigger and identifying a feedback event, an alert module 110 can be used to provide an alert to the clinician based upon the identified feedback event. The alert can be an audio alert, a visual alert displayed on a screen, or any other type of alert. The alert can also include information about the feedback event that identifies the feedback event to the clinician, the meaning of the feedback event, and/or information regarding how to adjust the fitting based upon the feedback event. Such information can be stored in a datastore 114 that is in electrical communication with the fitting assistance module 106. For example, the datastore 114 stores information about feedback events and/or instructions on how to adjust the fitting based upon the feedback event. In embodiments, the alert module 110 can determine whether or not to issue the alert based upon user preferences of the clinician. For example, the fitting assistance module 108 can be configured to provide more alerts to a clinician based on the clinician's level of experience. That is, the fitting assistance module 108 can issue an alert for every detected feedback event for a less experienced clinician while only issuing alerts for less common or more subtle feedback events for a more experienced clinician. As such, the determination can be based upon a user profile of the clinician stored or otherwise associated with the fitting assistance module 106.

The alert can be generated directly by the fitting assistance module in communication with output device(s) 118 or by another module communicating with the fitting assistance module. For example, the system can optionally include a fitting module 116 that a clinician uses to adjust a medical prosthesis and/or provide stimulation to a recipient to test the medical prosthesis during a fitting. In embodiments, the fitting module 116 can communicate stimulus information to the fitting assistance module 106 that the physiological analysis module analyzes in conjunction with identified triggers to determine a feedback event. The fitting module 106 can also receive instructions and/or data from the fitting assistance module 106 to generate an alert and/or display information to a clinician based upon an identified feedback event. Output device(s) 118 include any or all of a speaker, a display, a LED indicator, or any other type of suitable output devices known to the art.

As described above, the system 100 can be used to identify triggers produced by a recipient 102, determine a feedback event based upon the identified trigger in relation to a stimulus, and provide an alert to a clinician performing the fitting. Among other benefits, the system 100 aids a clinician in performing faster and more precise fittings of medical devices. While the system 100 is described as having discrete modules performing specific actions, one of skill in the art will appreciate that more or fewer modules can be employed to perform the functionality disclosed herein without departing from the embodiments disclosed herein. For example, the physiological analysis module 108 and the alert module 110 can be combined into a single module to identify feedback events and alert a clinician. The various modules described as part of the system 100 can be implemented as software, hardware, or a combination of software and hardware.

Figure 2:
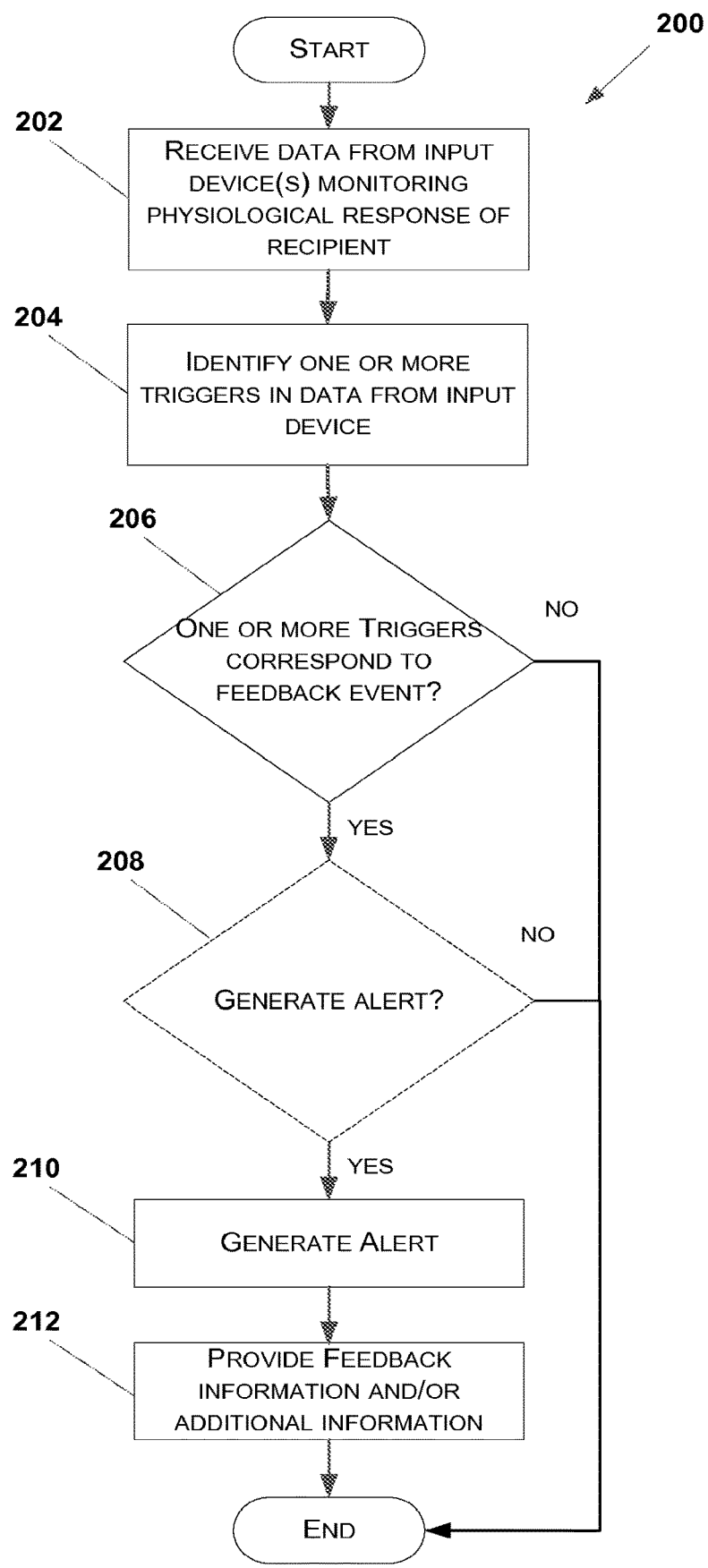
FIG. 2 is an embodiment of an exemplary method 200 to identify feedback events produced by a recipient during a fitting process.

FIG. 2 is an embodiment of an exemplary method 200 to identify feedback events produced by a recipient during a fitting process. In embodiments, the method 200 is performed by a module, such as the fitting assistance module 106 described with respect to FIG. 1. The method 200 can be performed by software, hardware, or a combination of software and hardware. Flow begins at operation 202 where the method 200 receives data from one or more input devices monitoring the physiological reactions of a recipient. For example, the method 200 can receive data from one or more cameras, a blood pressure device, a heart rate monitor, or any other type of device at operation 202. Flow continues to operation 204 where the data received at operation 202 is analyzed to determine if any triggers exist. In one embodiment, a trigger can be identified based upon a physiological measure meeting a certain threshold. For example, a trigger can be identified by an increase or decrease in heart rate. In other embodiments, a trigger can be identified by an action made by the recipient. For example, video data can be analyzed at operation 204 to identify an eye-blink reflex, a facial nerve stimulation, a sudden body movement, pupil dilation, or any other type of physical movement or reaction. Once a trigger is identified, flow continues to operation 206 where a determination is made as to whether the one or more triggers corresponds to a feedback event. In embodiments, the determination is made by comparing the trigger to one or more stimuli to determine whether the trigger is in response to the stimuli. For example, if the trigger occurred within temporal proximity (e.g., a proximate time) of a stimulus being applied to the recipient and/or medical prosthesis, a determination is made that the trigger is a result of the stimulus and not a random physiological event. Upon determining that the trigger results from the stimulus, a determination is made as to the type of feedback event that the trigger is related to. In embodiments, the determination is based on the type of trigger compared to the type of stimulus. In embodiments, a relationship between the trigger and the stimulus is not determined, no feedback event is identified and flow branches NO and the method 200 terminates.

If a feedback event is identified based upon the analysis described above, flow branches YES to optional operation 208, where a determination is made as to whether an alert should be generated. In embodiments, operation 208 is not required and the method 200 generates an alert when a feedback event is identified. In other embodiments, generation of an alert can depend upon a user profile associated with a clinician performing the fitting. For example, an alert can be generated for every detected feedback event for a less experienced clinician while alerts are only generated for less common or more subtle feedback events for an experienced clinician. As such, in embodiments, the determination is made by comparing the identified feedback event to a user profile. In embodiments, the user profile specifies the types of events for which alerts should or should not be generated. In such embodiments, the feedback event is compared to a list of events in the user profile to determine whether feedback event results in an alert for the particular user. If a determination is made that an alert should not be generated, flow branches NO and the method 200 terminates.

If the method 200 determines that an alert should be generated, flow branches YES to operation 210. At operation 210 an alert is generated, which can be an audible or visual alert. In embodiments, the method 200 can instruct an output device to generate the alert itself, or it can instruct another module to generate the alert. For example, the method 200 can be implemented as an independent module or piece of software from the fitting software. This allows the method 200 to be used with many different types of fitting software. In such embodiments, generating an alert at operation 210 comprises instructing the fitting software to generate an alert.

Upon generating the alert, flow continues to operation 212 where feedback information and/or additional information is provided by the method 200. In embodiments, the feedback information comprises information identifying the trigger. For example, the trigger can be displayed to the clinician in the form of physiological information such as the recipient's heart rate. In other embodiments, such as when the trigger is a physical movement, a picture or video can be displayed to the clinician illustrating the trigger. For example, if the trigger is an eye twitch, video of the recipient performing the eye twitch can be provided at operation 212. In one embodiment, the video or picture can be augmented by highlighting the specific trigger, such as highlighting the area around the movement, providing a zoomed-in playback focused on the area of movement, or using any other type of identifier to draw the clinician's attention to the trigger. In embodiments, information about the trigger can also comprise data about the meaning of the specific feedback event. The information can be displayed as text, an informative video, or audio information. In embodiments, additional information is also provided at operation 212. Additional information includes clinical instructions on how to adjust the medical prosthesis based upon the feedback event. In one embodiment, the information is immediately provided to the clinician. In other embodiments, the information is stored and provided to the clinician at a later time. For example, the information can be stored and played back later for training purposes. As described above with respect to operation 210 the device, software, hardware, application, or module performing the operation 200 can display information at operation 212 or can instruct another module, software, application, etc. to display information at operation 212.

While embodiments described herein describe determining whether one or more triggers correspond to a feedback event based upon proximity of the event to the one or more triggers, one of skill in the art will appreciate that the determination can be made using factors other than time. For example, there could be delayed physiological reactions exhibited by the recipient. For instance, the recipient may experience a slow change in taste in their mouth, but may make the mouthing action during a period where there was no stimulus. In embodiments, delayed reactions can also be identified as triggers even if the reactions are not within a specified proximity of a feedback event.

Figure 3:
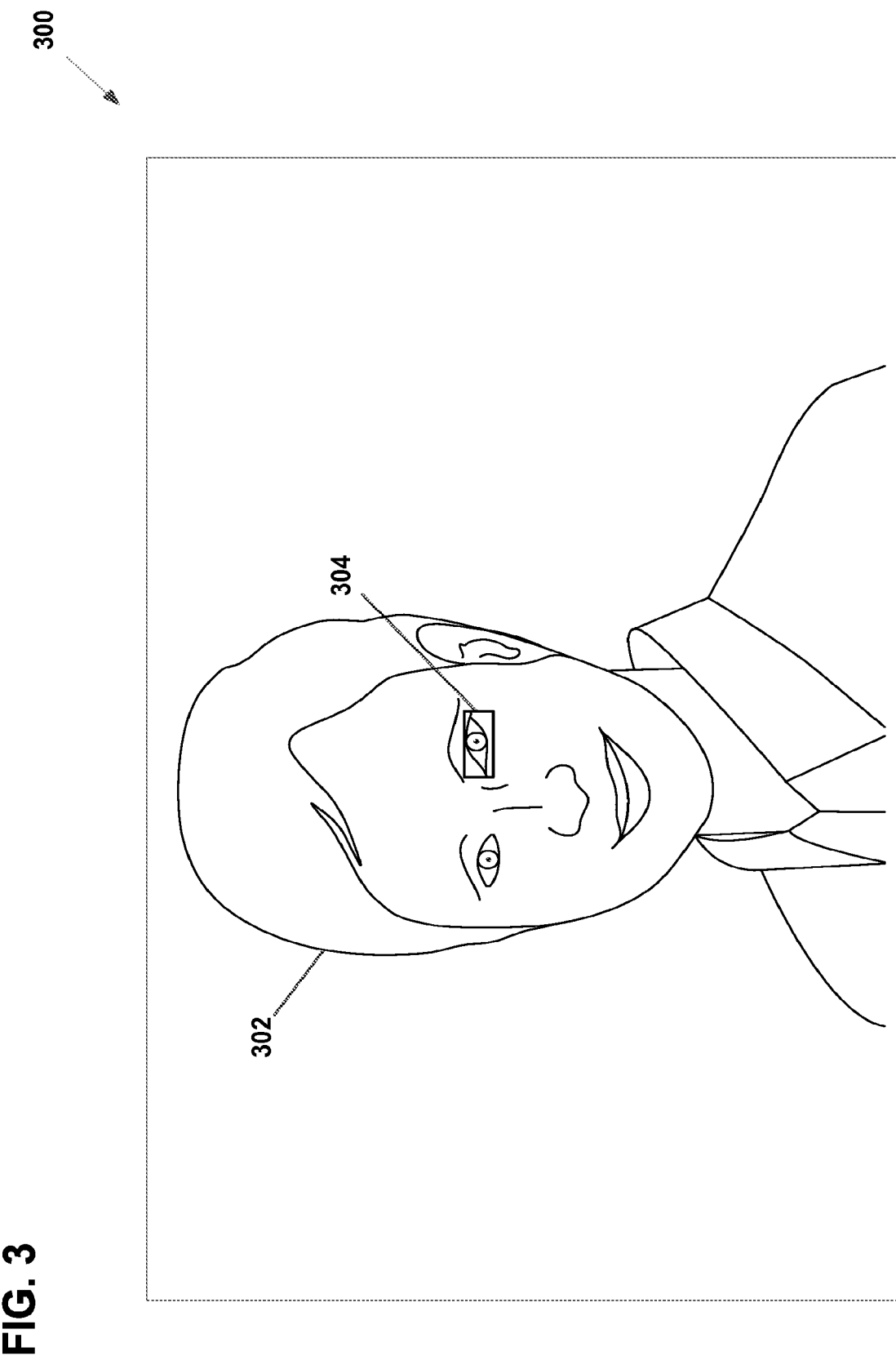
FIG. 3 is an embodiment of an exemplary graphical user interface 300 that can be employed to highlight a trigger captured by a camera.

FIG. 3 is an embodiment of an exemplary graphical user interface 300 that can be employed to highlight a trigger captured by a camera. In the illustrated embodiment, playback of the recipient 302 is displayed to the clinician. In the example embodiment, the trigger is an eye twitch. The user interface 300 overlays a box 304 around the twitching eye to draw the clinician's attention to the trigger. While an exemplary box is provided in FIG. 3 to draw the clinician's attention to the trigger, other types of indicators can be employed by the user interface such as, but not limited to, highlighting the trigger area in color or using another type of indicator.

Figure 4:
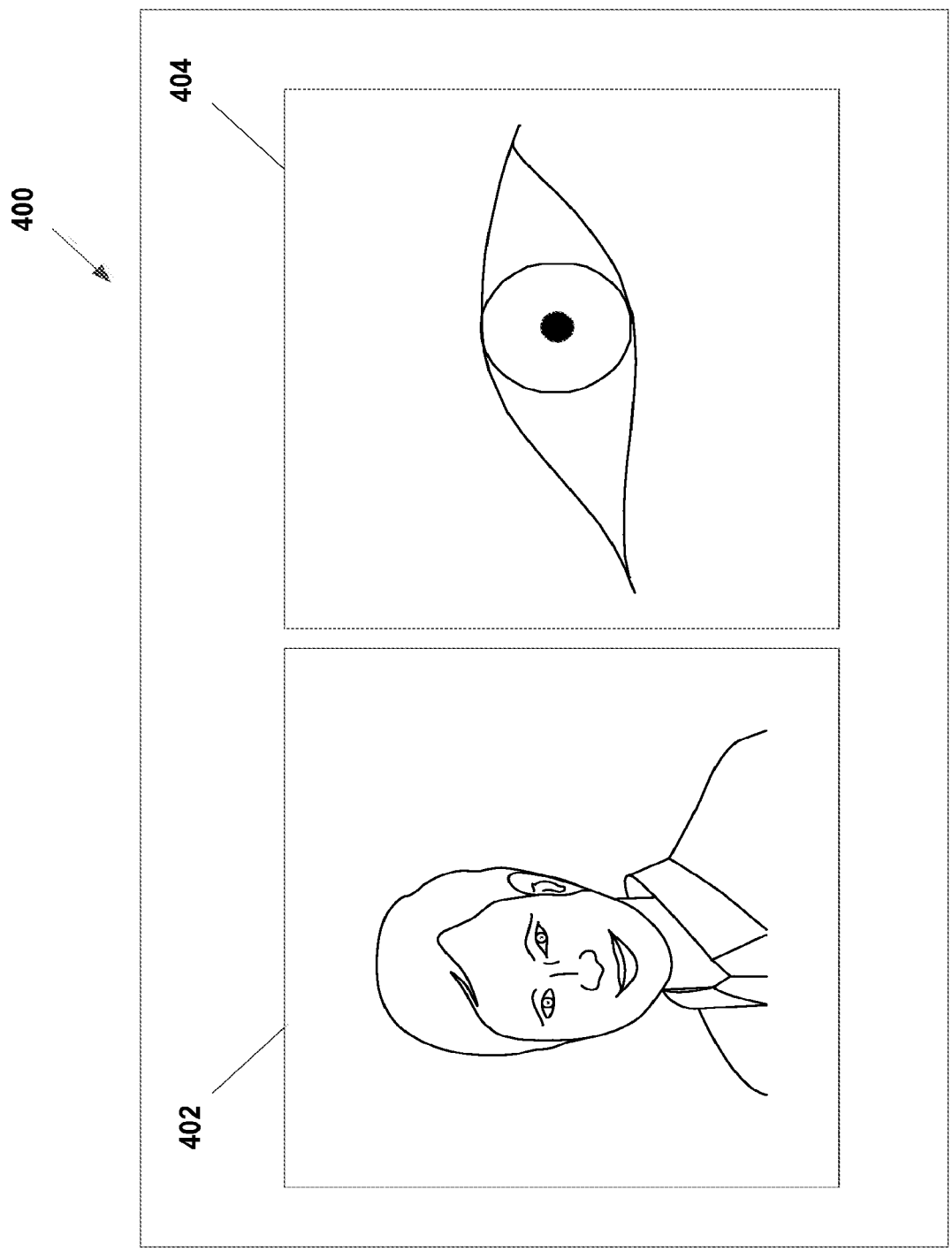
FIG. 4 is another embodiment of an exemplary graphical user interface 400 that can be employed to highlight a trigger captured by a camera.

FIG. 4 is another embodiment of an exemplary graphical user interface 400 that can be employed to highlight a trigger captured by a camera. User interface 400 includes a first pane 402 that provides a zoomed-out view of the recipient during the identified trigger and a second pane 404 that provides a zoomed-in view of the trigger area (a twitching eye in the illustrated example). This provides a clinician with a detailed view of the trigger as well as a larger view to provide context. In embodiments, the views can be still images or video playback. In embodiments, the video playback can be synchronized between the first pane 402 and the second pane 404.

Figure 5:
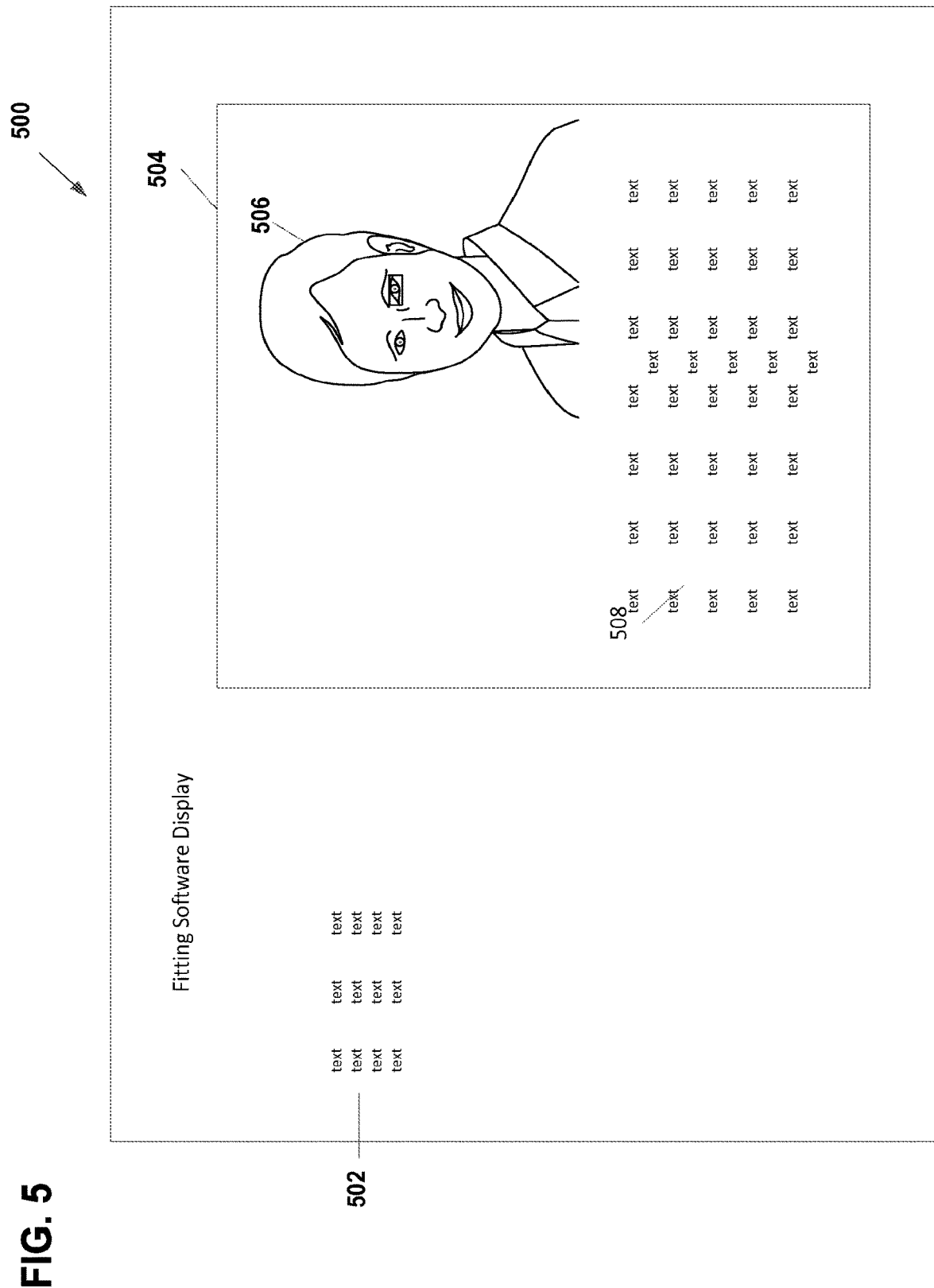
FIG. 5 illustrates an exemplary user interface 500 for displaying a trigger and providing feedback information and instruction to a clinician using fitting software.

FIG. 5 illustrates an exemplary user interface 500 for displaying a trigger and providing feedback information and clinical instruction to a clinician using fitting software. In the illustrated embodiment, the user interface for a fitting software is provided in a primary view 502. A secondary view 504 is displayed as an overlay with a first portion 506 illustrating the trigger and a second portion 508 comprising additional information about the feedback event and/or clinical information. Among other benefits, the illustrated embodiment of FIG. 5 ensures that a clinician focused on fitting software during the fitting process is alerted to the physiological cues of the recipient. While FIGS. 3-5 illustrate various embodiments of user interfaces that can be employed by the systems and methods disclosed herein, one of skill in the art will appreciate that different user interfaces can be employed without departing from the scope of this disclosure. For example, other user interfaces can be employed using different indicators to highlight triggers. The other types of interfaces can be visual or, in embodiments, audio playback if, for example, the trigger is an audio trigger. In other embodiments, rather than using a secondary view that is an overlay display to display feedback information over the user interface for fitting software, the secondary view can be in the form of a split screen interface that can be employed to display the feedback information next to the fitting software user interface. As such, the exemplary user interfaces provided herein are for illustrative purposes only and do not limit the scope of this disclosure.

Figure 6:
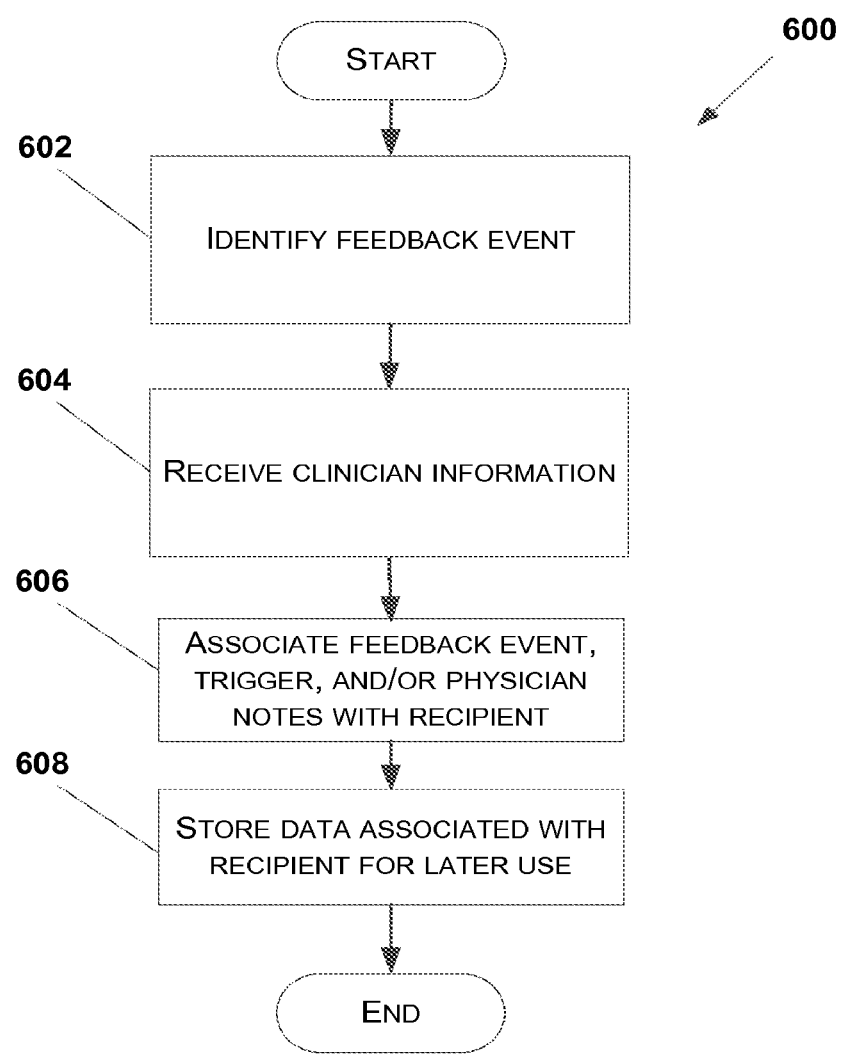
FIG. 6 is an embodiment of a method 600 of associating feedback event information with a recipient.

FIG. 6 is an embodiment of a method 600 of associating feedback event information with a recipient. Flow begins at operation 602 where a feedback event is identified. For example, the method 600 can be employed at operation 602 to identify feedback events. After identifying the feedback event, flow continues to operation 604 where additional information is received from a clinician performing the fitting. Additional information from the clinician comprises the clinician's notes and/or observations about the recipient related to the feedback event. In embodiments, the information received at operation 604 identifies that the identified trigger does not correspond to the feedback event typically associated with the identified trigger for the particular recipient. Such information can be used to disregard the trigger for a particular recipient in the future. In embodiments, the clinician need not provide additional information. In such embodiments, no information is received at operation 604.

Flow continues to operation 606 where the feedback event, trigger, and/or clinician information is associated with a particular recipient. The information can be associated with the particular recipient by employing a unique identifier to identify the recipient and using the unique identifier to associate the information with the particular recipient. Additional information can also be generated at the association step, such as the time and/or date that the fitting took place, the type of tests performed, etc. Flow then continues to operation 608 where the data associated with the recipient is stored for later use. As previously described with respect to FIG. 1, associating data with a particular user allows the embodiments disclosed herein to more accurately identify triggers for particular recipients. Additionally, machine learning algorithms can use the stored data as input to modify the embodiments disclosed herein to more accurately identify feedback events. In further embodiments, data captured for a specific recipient can be used to generate pre-emptive alerts. For example, the various systems and methods disclosed herein can identify that, in past sessions, a specific individual has exhibited a trigger in response to a specific stimulus. In such embodiments, the systems and methods disclosed herein can alert the clinician of the recipient's past behavior prior to the clinician applying the specific stimulus. For example, a message can be delivered to the clinician, such as: "On the past three occasions, John Smith has had an eye-twitch when you perform this action. Are you sure you want to perform this action?" In such embodiments, the system and method provides an alert that allows a clinician to avoid applying an uncomfortable stimulus to a recipient or to increase the vigilance of the clinician upon applying a stimulus known to cause a reaction in the recipient.

Figure 7:
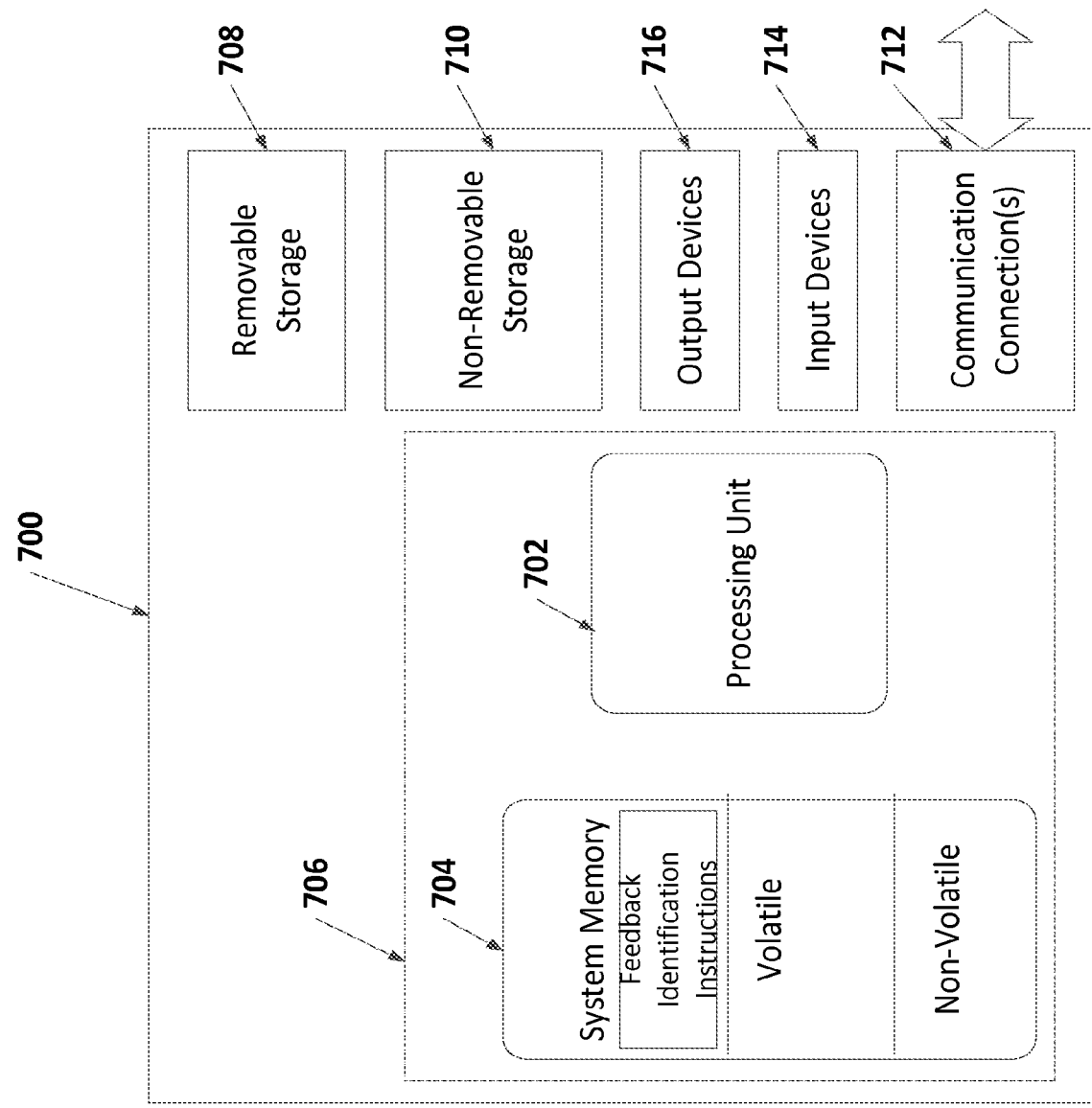
FIG. 7 illustrates one example of a suitable operating environment 700 in which one or more of the present examples can be implemented.

FIG. 7 illustrates one example of a suitable operating environment 700 in which one or more of the present embodiments can be implemented. This is only one example of a suitable operating environment and is not intended to suggest any limitation as to the scope of use or functionality. Other well-known computing systems, environments, and/or configurations that can be suitable for use include, but are not limited to, personal computers, server computers, handheld or laptop devices, multiprocessor systems, microprocessor-based systems, programmable consumer electronics such as smart phones, network PCs, minicomputers, mainframe computers, smartphones, tablets, distributed computing environments that include any of the above systems or devices, and the like.

In its most basic configuration, operating environment 700 typically includes at least one processing unit 702 and memory 704. Depending on the exact configuration and type of computing device, memory 704 (storing, among other things, instructions to implement and/or perform the modules and methods disclosed herein) can be volatile (such as RAM), non-volatile (such as ROM, flash memory, etc.), or some combination of the two. This most basic configuration is illustrated in FIG. 7 by dashed line 706. Further, environment 700 can also include storage devices (removable, 708, and/or non-removable, 710) including, but not limited to, magnetic or optical disks or tape. Similarly, environment 700 can also have input device(s) 714 such as touch screens, keyboard, mouse, pen, voice input, etc. and/or output device(s) 716 such as a display, speakers, printer, etc. Also included in the environment can be one or more communication connections, 712, such as LAN, WAN, point to point, Bluetooth, RF, etc.

Operating environment 700 typically includes at least some form of computer readable media. Computer readable media can be any available media that can be accessed by processing unit 702 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 700 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein comprise such modules or instructions executable by computer system 700 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 700 is part of a network that stores data in remote storage media for use by the computer system 700.

The embodiments described herein can be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices can be employed to perform the functionality disclosed herein without departing from the scope of the disclosure.

This disclosure described some embodiments of the present technology with reference to the accompanying drawings, in which only some of the possible embodiments were shown. Other aspects can, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments were described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A system comprising:
at least one video camera configured to:
record video data of a recipient while the recipient is stimulated by a medical device, wherein the video data includes pupil dilation data of the recipient and provide the video data to a computing device; and
the computing device comprising:
at least one processor; and
non-transitory computer storage media encoding computer executable instructions that, when executed by the at least one processor, cause the at least one processor to:
provide, using the video data, video playback of the recipient being stimulated by the medical device;
determine a feedback event based on the pupil dilation data;
generate at least one of audible alert or visible display indicative of the feedback event;
obtain additional information input by a user;
generate instructions for adjusting the medical device based on the feedback event and the additional information; and
cause an adjustment of the medical device based on the instructions.

2. The system of claim 1, wherein to determine the feedback event includes to determine that the pupil dilation data indicates that a physiological response occurred within a threshold amount of time of a clinical stimulation action.

3. The system of claim 1, wherein to cause the adjustment of the medical device based on the instructions includes to cause the adjustment immediately.

4. The system of claim 1, wherein the instructions, when executed by the at least one processor, further cause the at least one processor to:
store the instructions for adjusting the medical device.

5. A method comprising:
providing, with a hearing device, a stimulus to a recipient being fit with the hearing device;
receiving, with one or more processors, pupil dilation data from at least one camera recording pupil dilation data as the recipient is provided with the stimulus;
providing video playback of the recipient being stimulated by the hearing device using data from the at least one camera;
determining, with the one or more processors, a feedback event based on the pupil dilation data;
providing an indication of the feedback event to a user;
receiving an input from the user, wherein the input from the user is based on the indication of the feedback event and the video playback;
generating, with the one or more processors, instructions for adjusting the hearing device based on the feedback event and the input from the user; and
adjusting the hearing device using the instructions.

6. The method of claim 5, wherein determining the feedback event includes:
determining that the pupil dilation data indicates that a physiological response occurred within a threshold amount of time of the stimulus being provided.

7. The method of claim 5, further comprising:
generating, with the one or more processors, a preemptive alert to avoid providing a specific stimulation predicted to cause a reaction in the recipient.

8. The method of claim 7, wherein the preemptive alert is tailored to the recipient.

9. The method of claim 5, wherein the generating of the instructions includes generating clinical instructions describing how to adjust the hearing device;
and wherein the method further includes providing the clinical instructions to a clinician.

10. The method of claim 5, wherein the adjusting of the hearing device is performed by a clinician fitting the hearing device.

11. One or more non-transitory computer readable media having instructions stored thereon that, when executed by one or more processors, cause the one or more processors to perform steps comprising:
provide, with a hearing device, a stimulus to a recipient being fit with the hearing device;
receive pupil dilation data from at least one camera recording pupil dilation data as the recipient is provided with the stimulus;
provide video playback of the recipient being stimulated by the hearing device using data from the at least one camera;
determine a feedback event based on the pupil dilation data;
provide an indication of the feedback event to a user;
obtain additional information input by a user, wherein the input from the user is based on the indication of the feedback event and the video playback;
generate instructions for adjusting the medical device based on the feedback event and the additional information; and
cause an adjustment of the medical device based on the instructions.

12. The one or more non-transitory computer readable media of claim 11, wherein the instructions executed to determine the feedback event include instructions that, when executed, cause the one or more processors to:
determine that the pupil dilation data indicates that a physiological response occurred within a threshold amount of time of the stimulus being provided.

13. The one or more non-transitory computer readable media of claim 11, further comprising instructions that, when executed, cause the one or more processors to:
generate, a preemptive alert to avoid providing a specific stimulation predicted to cause a reaction in the recipient.

14. The one or more non-transitory computer readable media of claim 13, wherein the preemptive alert is tailored to the recipient.

* * * * *